(12) United States Patent
Van Breusegem et al.

(10) Patent No.: US 8,318,675 B2
(45) Date of Patent: Nov. 27, 2012

(54) CRUSTACEAN ANDROGENIC GLAND HORMONE, ASSOCIATED PEPTIDES, AND USE THEREOF

(75) Inventors: Frank Van Breusegem, Gent (BE); Jan Staelens, Rumbeke (BE); Marnik Vuylsteke, Gent (BE)

(73) Assignees: VIB VZW, Gent (BE); Universiteit Gent, Gent (BE); Moana Belgium N.V., Ternat (BE)

( * ) Notice: Subject to any disclaimer, the term of this patent is extended or adjusted under 35 U.S.C. 154(b) by 98 days.

(21) Appl. No.: 12/736,048

(22) PCT Filed: Mar. 5, 2009

(86) PCT No.: PCT/EP2009/052587
§ 371 (c)(1),
(2), (4) Date: Nov. 19, 2010

(87) PCT Pub. No.: WO2009/109615
PCT Pub. Date: Sep. 11, 2009

(65) Prior Publication Data
US 2011/0065638 A1     Mar. 17, 2011

Related U.S. Application Data

(60) Provisional application No. 61/033,830, filed on Mar. 5, 2008.

(51) Int. Cl.
*A61K 38/17* (2006.01)
*C07K 14/435* (2006.01)
(52) U.S. Cl. .................. 514/16.5; 530/350; 530/399
(58) Field of Classification Search .................. None
See application file for complete search history.

(56) References Cited

FOREIGN PATENT DOCUMENTS

| WO | WO 2007/122247 | 11/2007 |
|---|---|---|
| WO | WO 2009/109615 A1 | 9/2009 |

OTHER PUBLICATIONS

Sun et al., Developmental changes in structure and polypeptide profile of the androgenic gland of the freshwater prawn *Macrobrachium rosenbergii*, Aquaculture International, 2000, pp. 327-334, vol. 8, No. 4.
Sagi et al., The androgenic gland and monosex culture of freshwater prawn *Macrobrachium rosenbergii* (De Man): a biotechnological perspective. Aquaculture Research, 2005, pp. 231-237, vol. 36, No. 3.
Manor et al., Insulin and gender: An insulin-like gene expressed exclusively in the androgenic gland of the male crayfish, General and Comparative Endocrinology, 2006, pp. 326-336, vol. 150, No. 2.
Aflalo et al., A novel two-step procedure for mass production of all-male populations of the giant freshwater prawn *Macrobrachium rosenbergii*, Aquaculture, 2006, pp. 468-478, vol. 256, No. 1-4.
Okumura et al., Changes in gonadal development, androgenic gland cell structure, and hemolymph vitellogenin levels during male phase and sex change in laboratory-maintained protandric shrimp, Pandalus hypsinotus (Crustacea: Caridea: Pandalidae) Marine Biology, 2005, pp. 347-361, vol. 148, No. 2.
Rungsin et al., Production of all-male stock by neofemale technology of the Thai strain of freshwater prawn, *Macrobrachium rosenbergii*, Aquaculture, 2006, pp. 88-94, vol. 259, No. 1-4.

*Primary Examiner* — Christine J Saoud
(74) *Attorney, Agent, or Firm* — TraskBritt

(57) ABSTRACT

The invention relates to a crustacean androgenic gland hormone. More specifically, described are an androgenic gland hormone and associated peptides derived from *Penaeus monodon*, and their use to influence the sex ratio in prawn and shrimp cultures, and to set up monosex cultures. It is also related to the use of the hormone and associated peptides, associated gene or fragments thereof in sex determination.

12 Claims, 1 Drawing Sheet

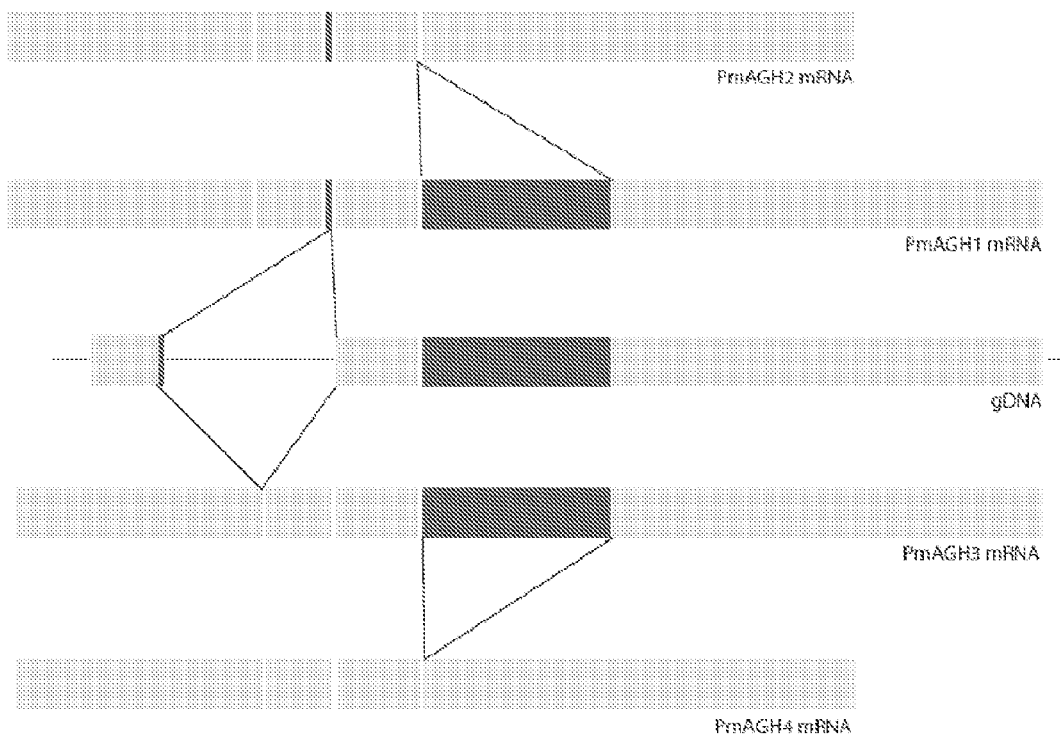

US 8,318,675 B2

SEQUENCE LISTING

```
<160> NUMBER OF SEQ ID NOS: 28

<210> SEQ ID NO 1
<211> LENGTH: 2091
<212> TYPE: DNA
<213> ORGANISM: Penaeus monodon

<400> SEQUENCE: 1
gaggtgctgc cacacacagg acagggcaag ttctctgccc ggccttaccc tgatccaaga      60
accattcaag gttgtgcgtg taccctcact ccttcacttt cccgtatcct ccccaccata     120
cccaccactc cagttctcca cctccaaccc tcctcagatc tctccaccaa tccctccaca     180 aaaccactc catcaaccct acgtatttgc taactcctcc acctccctc tatccacccc      240 tcctatccta ttatccctcc tccttttcca ctcttctcat agacacaaag aaaaaaatga     300
accaactcgc tgcctcacgc acctacggcc tcggcatgcc cactcagctg cttgtgggaa     360
tgctgatggt cctctccctg acttcgacgt caagctgcta caacgtcacg gggattcctg     420
ttgacttcga ctgcggtgac atcggcgata ccatgagtca catctgcaag acgtttccca     480
cagcccggcc tcactcgcga gtgtccaggt cagctgatac cgacgacctc tggcaggaca     540
cgagagcagg tcagaccacg cccattgacc tgcttcctcg ccagtaccgc ctgcatcccc     600
gggccttgaa tccgatgcga tatttcgaaa tggttagtca ggacctgata agagaccacc     660
tggtgagccc cgargccgcg cacgccctcg tcaagacatc crggaggcgc gcgaagagat     720
cctacaacgt gcaggatgag tgctgcaacc acgtgagcca gcggacgtgt gtggcggagg     780
agattctgga gtattgcgag gacccggtac cttagtctcc cctggcggtt tctgtcatat     840
gcgatgttct ctcwttatta cacttttttt gctaatgctt acagatatac agtatatgca     900
tagcgcattc tgataacaca tatgtatatt ttatakgtgt acaatgtgtg ttaaaacaaa     960
ttcattgtgt tctctctgtt tcacaaggta gaatataatc ctatcctttt gatagtaatt    1020
tactcgcata cacgcttgta aatcttgttt tcgtctcgtg tggttttgat ctacattctt    1080
cttcatgtat gatttctaga tgtgagagta agtaggcaag ttatctctcg aatgaaattc    1140
gaaatcaggc aaatcagtya ttaacatttc tcccttctgt ttccccagta cttctaaacc    1200
ttgaacctga cctgacctat ggccttccta acctctctaa gtggagtcgt cagtggtcca    1260
tggcccaccc atcctcctta caacagtctt cggtgacctg atcatatggc ctctccatcc    1320
tctcaatgac ctgacctcaa cccaygggtc cccccttctt taggccaagt ctttgcggac    1380
ctgacccaaa ccgaggcttc tctaaccctc ctctgatgag tttgtaataa aaataaccgg    1440
cctggtgacc caagttctca tgaatttgac ttaatctgca attaatgacc cgttagagtc    1500
```

-continued

```
ctttcaatga tgtctgccaa aagtagcgtt acattccatt tttctttcg aktawtaggc    1560 cccagagtaa ttcttgacct caactttcta aaaaaaaata ygtatattca grgcaagaac    1620
tattttcatt catgttctgt caatttctty ggcgtcataa tttctttcta tccttttatt    1680
aaacaaaata aataaaagat aaccatacat taacaaaggt gtgatacaaa gacataaaag    1740
atatcaaagt tcagtacttt ctttcgcttt ttctattttt atctttcgat tttccgaacg    1800
ttttaaagtt tctaactttt atcccyctgt aaaaataaag ttgacagacg ataataaaaa    1860
gcaataatgt tttagaatct attccttttt tgtgatcacc tgaatatctt ttttatatat    1920
acattatcgt attggaatca gatagatcag yacggyatat cagaattaat tcgtaataaa    1980
aaaatgcatt tcaataactg aatttccgat aaaaaaattt cmcctgtatc tgtcttttgc    2040
gaaacaataa aagcatttca aaatcgraaa aaaaaaaaaa aaaaaaaaaa a             2091
```

<210> SEQ ID NO 2
<211> LENGTH: 480
<212> TYPE: DNA
<213> ORGANISM: Penaeus monodon

<400> SEQUENCE: 2

```
atgcccactc agctgcttgt gggaatgctg atggtcctct ccctgacttc gacgtcaagc     60
tgctacaacg tcacggggat tcctgttgac ttcgactgcg gtgacatcgg cgataccatg    120
agtcacatct gcaagacgtt tcccacagcc cggcctcact cgcgagtgtc caggtcagct    180
gataccgacg acctctggca ggacacgaga gcaggtcaga ccacgcccat tgacctgctt    240
cctcgccagt accgcctgca tccccgggcc ttgaatccga tgcgatattt cgaaatggtt    300
agtcaggacc tgataagaga ccacctggtg agccccgarg ccgcgcacgc cctcgtcaag    360
acatccrgga ggcgcgcgaa gagatcctac aacgtgcagg atgagtgctg caaccacgtg    420
agccagcgga cgtgtgtggc ggaggagatt ctggagtatt gcgaggaccc ggtaccttag    480
```

<210> SEQ ID NO 3
<211> LENGTH: 159
<212> TYPE: PRT
<213> ORGANISM: Penaeus monodon

<400> SEQUENCE: 3

Met Pro Thr Gln Leu Leu Val Gly Met Leu Met Val Leu Ser Leu Thr
1               5                   10                  15

Ser Thr Ser Ser Cys Tyr Asn Val Thr Gly Ile Pro Val Asp Phe Asp
            20                  25                  30

Cys Gly Asp Ile Gly Asp Thr Met Ser His Ile Cys Lys Thr Phe Pro
        35                  40                  45

Thr Ala Arg Pro His Ser Arg Val Ser Arg Ser Ala Asp Thr Asp Asp
    50                  55                  60

Leu Trp Gln Asp Thr Arg Ala Gly Gln Thr Thr Pro Ile Asp Leu Leu
65                  70                  75                  80

Pro Arg Gln Tyr Arg Leu His Pro Arg Ala Leu Asn Pro Met Arg Tyr
                85                  90                  95

Phe Glu Met Val Ser Gln Asp Leu Ile Arg Asp His Leu Val Ser Pro
            100                 105                 110

Glu Ala His Ala Leu Val Lys Thr Ser Gly Arg Arg Ala Lys Arg
        115                 120                 125

Ser Tyr Asn Val Gln Asp Glu Cys Cys Asn His Val Ser Gln Arg Thr
    130                 135                 140

-continued

```
Cys Val Ala Glu Glu Ile Leu Glu Tyr Cys Glu Asp Pro Val Pro
145                 150                 155

<210> SEQ ID NO 4
<211> LENGTH: 1709
<212> TYPE: PRT
<213> ORGANISM: Penaeus monodon

<400> SEQUENCE: 4

Gly Ala Gly Gly Thr Gly Cys Thr Gly Cys Cys Ala Cys Ala Cys Ala
1               5                   10                  15

Cys Ala Gly Gly Ala Cys Ala Gly Gly Gly Cys Ala Ala Gly Thr Thr
            20                  25                  30

Cys Thr Cys Thr Gly Cys Cys Cys Gly Gly Cys Cys Thr Thr Ala Cys
        35                  40                  45

Cys Cys Thr Gly Ala Thr Cys Cys Ala Ala Gly Ala Ala Cys Cys Ala
    50                  55                  60

Thr Thr Cys Ala Ala Gly Gly Thr Thr Gly Thr Gly Cys Gly Thr Gly
65                  70                  75                  80

Thr Ala Cys Cys Cys Thr Cys Ala Cys Thr Cys Cys Thr Thr Cys Ala
                85                  90                  95

Cys Thr Thr Thr Cys Cys Cys Gly Thr Ala Thr Cys Cys Thr Cys Cys
            100                 105                 110

Cys Cys Ala Cys Cys Ala Thr Ala Cys Cys Cys Ala Cys Cys Ala Cys
        115                 120                 125

Thr Cys Cys Ala Gly Thr Thr Cys Thr Cys Cys Ala Cys Cys Thr Cys
    130                 135                 140

Cys Ala Ala Cys Cys Cys Thr Cys Cys Thr Cys Ala Gly Ala Thr Cys
145                 150                 155                 160

Thr Cys Thr Cys Cys Ala Cys Cys Ala Ala Thr Cys Cys Cys Thr Cys
                165                 170                 175

Cys Ala Cys Ala Ala Ala Ala Ala Cys Cys Ala Cys Thr Cys Cys Ala
            180                 185                 190

Thr Cys Ala Ala Cys Cys Cys Thr Ala Cys Gly Thr Ala Thr Thr Thr
        195                 200                 205

Gly Cys Thr Ala Ala Cys Thr Cys Cys Thr Cys Cys Ala Cys Cys Thr
    210                 215                 220

Cys Cys Cys Cys Thr Cys Thr Ala Thr Cys Cys Ala Cys Cys Cys Cys
225                 230                 235                 240

Thr Cys Cys Thr Ala Thr Cys Cys Thr Ala Thr Thr Ala Thr Cys Cys
                245                 250                 255

Cys Thr Cys Cys Thr Cys Cys Thr Thr Thr Thr Cys Cys Ala Cys Thr
            260                 265                 270

Cys Thr Thr Cys Thr Cys Ala Thr Ala Gly Ala Cys Ala Cys Ala Ala
        275                 280                 285

Ala Gly Ala Ala Ala Ala Ala Ala Ala Thr Gly Ala Ala Cys Cys Ala
    290                 295                 300

Ala Cys Thr Cys Gly Cys Thr Gly Cys Cys Thr Cys Ala Cys Gly Cys
305                 310                 315                 320

Ala Cys Cys Thr Ala Cys Gly Gly Cys Cys Thr Cys Gly Gly Cys Ala
                325                 330                 335

Thr Gly Cys Cys Cys Ala Cys Thr Cys Ala Gly Cys Thr Gly Cys Thr
            340                 345                 350

Thr Gly Thr Gly Gly Gly Ala Ala Thr Gly Cys Thr Gly Ala Thr Gly
        355                 360                 365
```

-continued

```
Gly Thr Cys Cys Thr Cys Thr Cys Cys Thr Gly Ala Cys Thr Thr
    370                 375                 380
Cys Gly Ala Cys Gly Thr Cys Ala Ala Gly Cys Thr Gly Cys Thr Ala
385                 390                 395                 400
Cys Ala Ala Cys Gly Thr Cys Ala Cys Gly Gly Gly Ala Thr Thr
                    405                 410                 415
Cys Cys Thr Gly Thr Thr Gly Ala Cys Thr Thr Cys Gly Ala Cys Thr
                420                 425                 430
Gly Cys Gly Gly Thr Gly Ala Cys Ala Thr Cys Gly Gly Cys Gly Ala
        435                 440                 445
Thr Ala Cys Cys Ala Thr Gly Ala Gly Thr Cys Ala Cys Ala Thr Cys
    450                 455                 460
Thr Gly Cys Ala Ala Gly Ala Cys Gly Thr Thr Cys Cys Ala
465                 470                 475                 480
Cys Ala Gly Cys Cys Gly Gly Cys Cys Thr Cys Ala Cys Thr Cys
                    485                 490                 495
Gly Cys Gly Ala Gly Thr Gly Thr Cys Ala Gly Gly Thr Cys Ala
                500                 505                 510
Gly Cys Thr Gly Ala Thr Ala Cys Cys Gly Ala Cys Gly Ala Cys Cys
        515                 520                 525
Thr Cys Thr Gly Gly Cys Ala Gly Gly Ala Cys Ala Cys Gly Ala Gly
    530                 535                 540
Ala Gly Cys Ala Gly Gly Thr Cys Ala Gly Ala Cys Cys Ala Cys Gly
545                 550                 555                 560
Cys Cys Cys Ala Thr Thr Gly Ala Cys Cys Thr Gly Cys Thr Thr Cys
                    565                 570                 575
Cys Thr Cys Gly Cys Cys Ala Gly Thr Ala Cys Cys Gly Cys Cys Thr
                580                 585                 590
Gly Cys Ala Thr Cys Cys Cys Gly Gly Cys Cys Thr Thr Gly
        595                 600                 605
Ala Ala Thr Cys Gly Ala Thr Gly Cys Gly Ala Thr Ala Thr Thr
    610                 615                 620
Thr Cys Gly Ala Ala Ala Thr Gly Gly Thr Thr Ala Gly Thr Cys Ala
625                 630                 635                 640
Gly Gly Ala Cys Cys Thr Gly Ala Thr Ala Ala Gly Ala Gly Ala Cys
                    645                 650                 655
Cys Ala Cys Cys Thr Gly Gly Thr Gly Ala Gly Cys Cys Cys Cys Gly
                660                 665                 670
Ala Arg Gly Cys Cys Gly Cys Gly Cys Ala Cys Gly Cys Cys Cys Thr
        675                 680                 685
Cys Gly Thr Cys Ala Ala Gly Ala Cys Ala Thr Cys Cys Arg Gly Gly
    690                 695                 700
Ala Gly Gly Cys Gly Cys Gly Cys Gly Ala Ala Gly Ala Gly Ala Thr
705                 710                 715                 720
Cys Cys Thr Ala Cys Ala Ala Cys Gly Thr Gly Cys Ala Gly Gly Ala
                    725                 730                 735
Thr Gly Ala Gly Thr Gly Cys Thr Gly Cys Ala Ala Cys Cys Ala Cys
                740                 745                 750
Gly Thr Gly Ala Gly Cys Cys Ala Cys Gly Gly Ala Cys Gly Thr
        755                 760                 765
Gly Thr Gly Thr Gly Gly Cys Gly Gly Ala Gly Gly Ala Gly Ala Thr
    770                 775                 780
Thr Cys Thr Gly Gly Ala Gly Thr Ala Thr Thr Gly Cys Gly Ala Gly
785                 790                 795                 800
```

-continued

Gly Ala Cys Cys Cys Gly Thr Ala Cys Thr Thr Cys Thr Ala Ala Ala
              805                 810                 815

Cys Cys Thr Thr Gly Ala Ala Cys Cys Thr Gly Ala Cys Cys Thr Gly
          820                 825                 830

Ala Cys Cys Thr Ala Thr Gly Gly Cys Thr Thr Cys Cys Thr Ala
          835                 840                 845

Ala Cys Cys Thr Cys Thr Cys Thr Ala Ala Gly Thr Gly Ala Gly
          850                 855                 860

Thr Cys Gly Thr Cys Ala Gly Thr Gly Gly Thr Cys Cys Ala Thr Gly
865               870                 875                 880

Gly Cys Cys Cys Ala Cys Cys Ala Thr Cys Cys Thr Cys Cys Thr
          885                 890                 895

Thr Ala Cys Ala Ala Cys Ala Gly Thr Cys Thr Thr Cys Gly Gly Thr
          900                 905                 910

Gly Ala Cys Cys Thr Gly Ala Thr Cys Ala Thr Ala Thr Gly Gly Cys
          915                 920                 925

Cys Thr Cys Thr Cys Cys Ala Thr Cys Cys Thr Cys Thr Cys Ala Ala
          930                 935                 940

Thr Gly Ala Cys Cys Thr Gly Ala Cys Cys Thr Cys Ala Ala Cys Cys
945               950                 955                 960

Cys Ala Tyr Gly Gly Gly Thr Cys Cys Cys Cys Cys Thr Thr Cys
              965                 970                 975

Thr Thr Thr Ala Gly Gly Cys Cys Ala Ala Gly Thr Cys Thr Thr Thr
              980                 985                 990

Gly Cys Gly Gly Ala Cys Cys Thr  Gly Ala Cys Cys Cys Ala Ala Ala
              995                1000                1005

Cys Cys  Gly Ala Gly Gly Cys  Thr Thr Cys Thr Cys  Thr Ala Ala
         1010                 1015                 1020

Cys Cys  Cys Thr Cys Cys Thr  Cys Thr Gly Ala Thr  Gly Ala Gly
         1025                 1030                 1035

Thr Thr  Thr Gly Thr Ala Ala  Thr Ala Ala Ala  Ala Thr Ala
         1040               1045               1050

Ala Cys  Cys Gly Gly Cys Cys  Thr Gly Gly Thr Gly  Ala Cys Cys
         1055                1060                 1065

Cys Ala  Ala Gly Thr Thr Cys  Thr Cys Ala Thr Gly  Ala Ala Thr
         1070                1075                 1080

Thr Thr  Gly Ala Cys Thr Thr  Ala Ala Thr Cys Thr  Gly Cys Ala
         1085                1090                 1095

Ala Thr  Thr Ala Ala Thr Gly  Ala Cys Cys Cys Gly  Thr Thr Ala
         1100                1105                 1110

Gly Ala  Gly Thr Cys Cys Thr  Thr Thr Cys Ala Ala  Thr Gly Ala
         1115                1120                 1125

Thr Gly  Thr Cys Thr Gly Cys  Cys Ala Ala Ala Ala  Gly Thr Ala
         1130                1135                 1140

Gly Cys  Gly Thr Thr Ala Cys  Ala Thr Thr Cys Cys  Ala Thr Thr
         1145                1150                 1155

Thr Thr  Thr Cys Thr Thr Thr  Thr Cys Gly Ala Lys  Thr Ala Trp
         1160                1165                 1170

Thr Ala  Gly Gly Cys Cys Cys  Ala Gly Ala Gly  Thr Ala Ala
         1175                1180              1185

Thr Thr  Cys Thr Thr Gly Ala  Cys Cys Thr Cys Ala  Ala Cys Thr
         1190                1195                 1200

Thr Thr  Cys Thr Ala Ala Ala  Ala Ala Ala Ala Ala  Ala Thr Ala

-continued

```
                1205                1210                1215

Tyr Gly Thr Ala Thr Ala Thr Thr Cys Ala Gly Arg Gly Cys Ala
    1220                1225                1230

Ala Gly Ala Ala Cys Thr Ala Thr Thr Thr Cys Ala Thr Thr
    1235                1240                1245

Cys Ala Thr Gly Thr Thr Cys Thr Gly Thr Cys Ala Ala Thr Thr
    1250                1255                1260

Thr Cys Thr Thr Tyr Gly Gly Cys Gly Thr Cys Ala Thr Ala Ala
    1265                1270                1275

Thr Thr Thr Cys Thr Thr Cys Thr Ala Thr Cys Cys Thr Thr
    1280                1285                1290

Thr Thr Ala Thr Thr Ala Ala Ala Cys Ala Ala Ala Ala Thr Ala
    1295                1300                1305

Ala Ala Thr Ala Ala Ala Ala Gly Ala Thr Ala Ala Cys Cys Ala
    1310                1315                1320

Thr Ala Cys Ala Thr Thr Ala Ala Cys Ala Ala Ala Gly Gly Thr
    1325                1330                1335

Gly Thr Gly Ala Thr Ala Cys Ala Ala Ala Gly Ala Cys Ala Thr
    1340                1345                1350

Ala Ala Ala Ala Gly Ala Thr Ala Thr Cys Ala Ala Ala Gly Thr
    1355                1360                1365

Thr Cys Ala Gly Thr Ala Cys Thr Thr Thr Cys Thr Thr Thr Cys
    1370                1375                1380

Gly Cys Thr Thr Thr Thr Thr Cys Thr Ala Thr Thr Thr Thr Thr
    1385                1390                1395

Ala Thr Cys Thr Thr Thr Cys Gly Ala Thr Thr Thr Thr Cys Cys
    1400                1405                1410

Gly Ala Ala Cys Gly Thr Thr Thr Ala Ala Ala Gly Thr Thr
    1415                1420                1425

Thr Cys Thr Ala Ala Cys Thr Thr Thr Thr Ala Thr Cys Cys Cys
    1430                1435                1440

Tyr Cys Thr Gly Thr Ala Ala Ala Ala Ala Thr Ala Ala Ala Gly
    1445                1450                1455

Thr Thr Gly Ala Cys Ala Gly Ala Cys Gly Ala Thr Ala Ala Thr
    1460                1465                1470

Ala Ala Ala Ala Ala Gly Cys Ala Ala Thr Ala Ala Thr Gly Thr
    1475                1480                1485

Thr Thr Thr Ala Gly Ala Ala Thr Cys Thr Ala Thr Thr Cys Cys
    1490                1495                1500

Thr Thr Thr Thr Thr Thr Gly Thr Gly Ala Thr Cys Ala Cys Cys
    1505                1510                1515

Thr Gly Ala Ala Thr Ala Thr Cys Thr Thr Thr Thr Thr Ala
    1520                1525                1530

Thr Ala Thr Ala Thr Ala Cys Ala Thr Thr Ala Thr Cys Gly Thr
    1535                1540                1545

Ala Thr Thr Gly Gly Ala Ala Thr Cys Ala Gly Ala Thr Ala Gly
    1550                1555                1560

Ala Thr Cys Ala Gly Tyr Ala Cys Gly Gly Tyr Ala Thr Ala Thr
    1565                1570                1575

Cys Ala Gly Ala Ala Thr Thr Ala Ala Thr Thr Cys Gly Thr Ala
    1580                1585                1590

Ala Thr Ala Ala Ala Ala Ala Ala Ala Thr Gly Cys Ala Thr Thr
    1595                1600                1605
```

```
Thr Cys Ala Ala Thr Ala Ala Cys Thr Gly Ala Ala Thr Thr Thr
    1610            1615                1620

Cys Cys Gly Ala Thr Ala Ala Ala Ala Ala Ala Thr Thr Thr
    1625            1630                1635

Cys Met Cys Cys Thr Gly Thr Ala Thr Cys Thr Gly Thr Cys Thr
    1640            1645                1650

Thr Thr Thr Gly Cys Gly Ala Ala Cys Ala Ala Thr Ala Ala
    1655            1660                1665

Ala Ala Gly Cys Ala Thr Thr Thr Cys Ala Ala Ala Thr Cys
    1670            1675                1680

Gly Arg Ala Ala Ala Ala Ala Ala Ala Ala Ala Ala Ala
    1685            1690                1695

Ala Ala Ala Ala Ala Ala Ala Ala Ala Ala Ala
    1700            1705

<210> SEQ ID NO 5
<211> LENGTH: 480
<212> TYPE: DNA
<213> ORGANISM: Penaeus monodon

<400> SEQUENCE: 5
atgcccactc agctgcttgt gggaatgctg atggtcctct ccctgacttc gacgtcaagc    60
tgctacaacg tcacggggat tcctgttgac ttcgactgcg gtgacatcgg cgataccatg   120
agtcacatct gcaagacgtt tcccacagcc cggcctcact cgcgagtgtc caggtcagct   180
gataccgacg acctctggca ggacacgaga gcaggtcaga ccacgcccat tgacctgctt   240
cctcgccagt accgcctgca tccccgggcc ttgaatccga tgcgatattt cgaaatggtt   300
agtcaggacc tgataagaga ccacctggtg agccccgarg ccgcgcacgc cctcgtcaag   360
acatccrgga ggcgcgcgaa gagatcctac aacgtgcagg atgagtgctg caaccacgtg   420
agccagcgga cgtgtgtggc ggaggagatt ctggagtatt gcgaggaccc gtacttctaa   480

<210> SEQ ID NO 6
<211> LENGTH: 159
<212> TYPE: PRT
<213> ORGANISM: Penaeus monodon

<400> SEQUENCE: 6

Met Pro Thr Gln Leu Leu Val Gly Met Leu Met Val Leu Ser Leu Thr
1               5                   10                  15

Ser Thr Ser Ser Cys Tyr Asn Val Thr Gly Ile Pro Val Asp Phe Asp
            20                  25                  30

Cys Gly Asp Ile Gly Asp Thr Met Ser His Ile Cys Lys Thr Phe Pro
        35                  40                  45

Thr Ala Arg Pro His Ser Arg Val Ser Arg Ser Ala Asp Thr Asp Asp
    50                  55                  60

Leu Trp Gln Asp Thr Arg Ala Gly Gln Thr Thr Pro Ile Asp Leu Leu
65                  70                  75                  80

Pro Arg Gln Tyr Arg Leu His Pro Arg Ala Leu Asn Pro Met Arg Tyr
                85                  90                  95

Phe Glu Met Val Ser Gln Asp Leu Ile Arg Asp His Leu Val Ser Pro
            100                 105                 110

Glu Ala Ala His Ala Leu Val Lys Thr Ser Gly Arg Arg Ala Lys Arg
        115                 120                 125

Ser Tyr Asn Val Gln Asp Glu Cys Cys Asn His Val Ser Gln Arg Thr
    130                 135                 140
```

Cys Val Ala Glu Glu Ile Leu Glu Tyr Cys Glu Asp Pro Tyr Phe
145                 150                 155

<210> SEQ ID NO 7
<211> LENGTH: 2082
<212> TYPE: DNA
<213> ORGANISM: Penaeus monodon

<400> SEQUENCE: 7

| | | | | | | |
|---|---|---|---|---|---|---|
| gaggtgctgc | cacacacagg | acagggcaag | ttctctgccc | ggccttaccc | tgatccaaga | 60 |
| accattcaag | gttgtgcgtg | taccctcact | ccttcacttt | cccgtatcct | ccccaccata | 120 |
| cccaccactc | cagttctcca | cctccaaccc | tcctcagatc | tctccaccaa | tccctccaca | 180 |
| aaaaccactc | catcaaccct | acgtatttgc | taactcctcc | acctcccctc | tatccacccc | 240 |
| tcctatccta | ttatccctcc | tccttttcca | ctcttctcat | agacacaaag | aaaaaaatga | 300 |
| accaactcgc | tgcctcacgc | acctacggct | cggcatgcc | cactcagctg | cttgtgggaa | 360 |
| tgctgatggt | cctctccctg | acttcgacgt | caagctgcta | caacgtcacg | gggattcctg | 420 |
| ttgacttcga | ctgcggtgac | atcggcgata | ccatgagtca | catctgcaag | acgtttccca | 480 |
| cagcccggcc | tcactcgcga | gtgtccaggt | cagctgatac | cgacgacctc | tggcaggaca | 540 |
| cgagagcagg | tcagaccacg | cccattgacc | tgcttcctcg | ccagtaccgc | ctgcatcccc | 600 |
| gggccttgaa | tccgatgcga | tatttcgaaa | tggacctgat | aagagaccac | ctggtgagcc | 660 |
| ccgargccgc | gcacgccctc | gtcaagacat | ccrggaggcg | cgcgaagaga | tcctacaacg | 720 |
| tgcaggatga | gtgctgcaac | cacgtgagcc | agcggacgtg | tgtggcggag | gagattctgg | 780 |
| agtattgcga | ggacccggta | ccttagtctc | ccctggcggt | ttctgtcata | tgcgatgttc | 840 |
| tctcwttatt | acactttttt | tgctaatgct | tacagatata | cagtatatgc | atagcgcatt | 900 |
| ctgataacac | atatgtatat | tttatakgtg | tacaatgtgt | gttaaaacaa | attcattgtg | 960 |
| ttctctctgt | ttcacaaggt | agaatataat | cctatccttt | tgatagtaat | ttactcgcat | 1020 |
| acacgcttgt | aaatcttgtt | ttcgtctcgt | gtggttttga | tctacattct | tcttcatgta | 1080 |
| tgatttctag | atgtgagagt | aagtaggcaa | gttatctctc | gaatgaaatt | cgaaatcagg | 1140 |
| caaatcagty | attaacattt | ctcccttctg | tttccccagt | acttctaaac | cttgaacctg | 1200 |
| acctgaccta | tggccttcct | aacctctcta | agtggagtcg | tcagtggtcc | atggcccacc | 1260 |
| catcctcctt | acaacagtct | tcggtgacct | gatcatatgg | cctctccatc | ctctcaatga | 1320 |
| cctgacctca | acccaygggt | ccccccttct | ttaggccaag | tctttgcgga | cctgacccaa | 1380 |
| accgaggctt | ctctaaccct | cctctgatga | gtttgtaata | aaaataaccg | gcctggtgac | 1440 |
| ccaagttctc | atgaatttga | cttaatctgc | aattaatgac | ccgttagagt | cctttcaatg | 1500 |
| atgtctgcca | aaagtagcgt | tacattccat | ttttcttttc | gaktawtagg | ccccagagta | 1560 |
| attcttgacc | tcaactttct | aaaaaaaaat | aygtatattc | agrgcaagaa | ctattttcat | 1620 |
| tcatgttctg | tcaatttctt | yggcgtcata | atttctttct | atcctttat | taaacaaaat | 1680 |
| aaataaaaga | taaccataca | ttaacaaagg | tgtgatacaa | agacataaaa | gatatcaaag | 1740 |
| ttcagtactt | tctttcgctt | tttctatttt | tatctttcga | ttttccgaac | gttttaaagt | 1800 |
| ttctaacttt | tatcccyctg | taaaaataaa | gttgacagac | gataataaaa | agcaataatg | 1860 |
| ttttagaatc | tattccttt | ttgtgatcac | ctgaatatct | ttttatata | tacattatcg | 1920 |
| tattggaatc | agatagatca | gyacggyata | tcagaattaa | ttcgtaataa | aaaatgcat | 1980 |
| ttcaataact | gaatttccga | taaaaaaatt | tcmcctgtat | ctgtcttttg | cgaaacaata | 2040 |
| aaagcatttc | aaaatcgraa | aaaaaaaaaa | aaaaaaaaaa | aa | | 2082 |

<210> SEQ ID NO 8
<211> LENGTH: 471
<212> TYPE: DNA
<213> ORGANISM: Penaeus monodon

<400> SEQUENCE: 8

```
atgcccactc agctgcttgt gggaatgctg atggtcctct ccctgacttc gacgtcaagc      60
tgctacaacg tcacggggat tcctgttgac ttcgactgcg gtgacatcgg cgataccatg     120
agtcacatct gcaagacgtt tcccacagcc cggcctcact cgcgagtgtc caggtcagct     180
gataccgacg acctctggca ggacacgaga gcaggtcaga ccacgcccat tgacctgctt     240
cctcgccagt accgcctgca tccccgggcc ttgaatccga tgcgatattt cgaaatggac     300
ctgataagag accacctggt gagccccgar gccgcgcacg ccctcgtcaa gacatccrgg     360
aggcgcgcga agagatccta caacgtgcag gatgagtgct gcaaccacgt gagccagcgg     420
acgtgtgtgg cggaggagat tctggagtat tgcgaggacc cggtaccttag             471
```

<210> SEQ ID NO 9
<211> LENGTH: 156
<212> TYPE: PRT
<213> ORGANISM: Penaeus monodon

<400> SEQUENCE: 9

Met Pro Thr Gln Leu Leu Val Gly Met Leu Met Val Leu Ser Leu Thr
1               5                   10                  15

Ser Thr Ser Ser Cys Tyr Asn Val Thr Gly Ile Pro Val Asp Phe Asp
            20                  25                  30

Cys Gly Asp Ile Gly Asp Thr Met Ser His Ile Cys Lys Thr Phe Pro
        35                  40                  45

Thr Ala Arg Pro His Ser Arg Val Ser Arg Ser Ala Asp Thr Asp Asp
    50                  55                  60

Leu Trp Gln Asp Thr Arg Ala Gly Gln Thr Thr Pro Ile Asp Leu Leu
65                  70                  75                  80

Pro Arg Gln Tyr Arg Leu His Pro Arg Ala Leu Asn Pro Met Arg Tyr
                85                  90                  95

Phe Glu Met Asp Leu Ile Arg Asp His Leu Val Ser Pro Glu Ala Ala
            100                 105                 110

His Ala Leu Val Lys Thr Ser Gly Arg Arg Ala Lys Arg Ser Tyr Asn
        115                 120                 125

Val Gln Asp Glu Cys Cys Asn His Val Ser Gln Arg Thr Cys Val Ala
    130                 135                 140

Glu Glu Ile Leu Glu Tyr Cys Glu Asp Pro Val Pro
145                 150                 155

<210> SEQ ID NO 10
<211> LENGTH: 1700
<212> TYPE: DNA
<213> ORGANISM: Penaeus monodon

<400> SEQUENCE: 10

```
gaggtgctgc cacacacagg acagggcaag ttctctgccc ggccttaccc tgatccaaga      60
accattcaag gttgtgcgtg taccctcact ccttcacttt cccgtatcct ccccaccata     120
cccaccactc cagttctcca cctccaaccc tcctcagatc tctccaccaa tccctccaca     180
aaaaccactc catcaaccct acgtatttgc taactcctcc acctcccctc tatccacccc     240
tcctatccta ttatccctcc tccttttcca ctcttctcat agacacaaag aaaaaaatga     300
```

-continued

```
accaactcgc tgcctcacgc acctacggcc tcggcatgcc cactcagctg cttgtgggaa    360
tgctgatggt cctctccctg acttcgacgt caagctgcta caacgtcacg gggattcctg    420
ttgacttcga ctgcggtgac atcggcgata ccatgagtca catctgcaag acgtttccca    480
cagcccggcc tcactcgcga gtgtccaggt cagctgatac cgacgacctc tggcaggaca    540
cgagagcagg tcagaccacg cccattgacc tgcttcctcg ccagtaccgc ctgcatcccc    600
gggccttgaa tccgatgcga tatttcgaaa tggacctgat aagagaccac ctggtgagcc    660
ccgargccgc gcacgccctc gtcaagacat ccrggaggcg cgcgaagaga tcctacaacg    720
tgcaggatga gtgctgcaac cacgtgagcc agcggacgtg tgtggcggag gagattctgg    780
agtattgcga ggacccgtac ttctaaacct gaacctgac  ctgacctatg gccttcctaa    840
cctctctaag tggagtcgtc agtggtccat ggcccaccca tcctccttac aacagtcttc    900
ggtgacctga tcatatggcc tctccatcct ctcaatgacc tgacctcaac ccayggtcc     960
cccttcttt aggccaagtc tttgcggacc tgacccaaac cgaggcttct ctaaccctcc     1020
tctgatgagt ttgtaataaa ataaccggc  ctggtgaccc aagttctcat gaatttgact    1080
taatctgcaa ttaatgaccc gttagagtcc tttcaatgat gtctgccaaa gtagcgtta     1140
cattccattt ttcttttcga ktawtaggcc ccagagtaat tcttgacctc aactttctaa    1200
aaaaaaatay gtatattcag rgcaagaact attttcattc atgttctgtc aatttcttyg    1260
gcgtcataat ttctttctat cctttttatta aacaaaataa ataaaagata accatacatt   1320
aacaaaggtg tgatacaaag acataaaaga tatcaaagtt cagtactttc tttcgctttt   1380
tctattttta tctttcgatt ttccgaacgt tttaaagttt ctaacttta  tcccyctgta    1440
aaaataaagt tgacagacga taataaaaag caataatgtt ttagaatcta ttcctttttt    1500
gtgatcacct gaatatcttt tttatatata cattatcgta ttggaatcag atagatcagy    1560
acggyatatc agaattaatt cgtaataaaa aaatgcattt caataactga atttccgata    1620
aaaaaatttc mcctgtatct gtcttttgcg aaacaataaa agcatttcaa aatcgraaaa    1680
aaaaaaaaaa aaaaaaaaa                                                  1700
```

<210> SEQ ID NO 11
<211> LENGTH: 471
<212> TYPE: DNA
<213> ORGANISM: Penaeus monodon

<400> SEQUENCE: 11

```
atgcccactc agctgcttgt gggaatgctg atggtcctct ccctgacttc gacgtcaagc     60
tgctacaacg tcacggggat tcctgttgac ttcgactgcg gtgacatcgg cgataccatg    120
agtcacatct gcaagacgtt tcccacagcc cggcctcact cgcgagtgtc caggtcagct    180
gataccgacg acctctggca ggacacgaga gcaggtcaga ccacgcccat tgacctgctt    240
cctcgccagt accgcctgca tccccgggcc ttgaatccga tgcgatattt cgaaatggac    300
ctgataagag accacctggt gagccccgar gccgcgcacg ccctcgtcaa gacatccrgg    360
aggcgcgcga agagatccta caacgtgcag gatgagtgct gcaaccacgt gagccagcgg    420
acgtgtgtgg cggaggagat tctggagtat tgcgaggacc cgtacttcta a              471
```

<210> SEQ ID NO 12
<211> LENGTH: 156
<212> TYPE: PRT
<213> ORGANISM: Penaeus monodon

<400> SEQUENCE: 12

```
Met Pro Thr Gln Leu Leu Val Gly Met Leu Met Val Leu Ser Leu Thr
1               5                   10                  15

Ser Thr Ser Ser Cys Tyr Asn Val Thr Gly Ile Pro Val Asp Phe Asp
            20                  25                  30

Cys Gly Asp Ile Gly Asp Thr Met Ser His Ile Cys Lys Thr Phe Pro
        35                  40                  45

Thr Ala Arg Pro His Ser Arg Val Ser Arg Ser Ala Asp Thr Asp Asp
    50                  55                  60

Leu Trp Gln Asp Thr Arg Ala Gly Gln Thr Thr Pro Ile Asp Leu Leu
65              70                  75                  80

Pro Arg Gln Tyr Arg Leu His Pro Arg Ala Leu Asn Pro Met Arg Tyr
                85                  90                  95

Phe Glu Met Asp Leu Ile Arg Asp His Leu Val Ser Pro Glu Ala Ala
            100                 105                 110

His Ala Leu Val Lys Thr Ser Gly Arg Arg Ala Lys Arg Ser Tyr Asn
        115                 120                 125

Val Gln Asp Glu Cys Cys Asn His Val Ser Gln Arg Thr Cys Val Ala
    130                 135                 140

Glu Glu Ile Leu Glu Tyr Cys Glu Asp Pro Tyr Phe
145                 150                 155

<210> SEQ ID NO 13
<211> LENGTH: 2008
<212> TYPE: DNA
<213> ORGANISM: Penaeus monodon

<400> SEQUENCE: 13
aaatcaaact gtatttttat ctcaaccaca aaacatccca acaagcagac agtgccttct     60
ctttccctta cagtgtccag gtcagctgat accgacgacc tctggcagga cacgagagca    120
ggtcagacca cgcccattga cctgcttcct cgccagtacc gcctgcatcc ccgggccttg    180
aatccgatgc gatatttcga atggttagt caggtaacag gtatttctta ttaattgtaa    240
caccattatc acaaatatct gataatatta agtatctgca agttcctatt cttctgtggt    300
gttcgtgatt cttaattgca tagcattatt ttcagttctc agataatatt gcatactgac    360
gtgcgctaca gtttaattac ccttcatata taacatcact tttatgtaat cttaccttgt    420
gacatataga aacatacaac gatagtctgc ccactaagta cctgcgaggt agacggttct    480
atttctgcag tactacataa tatatacaca aaatagactc tagtacacga aaggattcct    540
gccatgccac aggacctgat aagagaccac ctggtgagcc ccgargccgc gcacgccctc    600
gtcaagacat ccrggaggcg cgcgaagaga tcctacaacg tgcaggatga gtgctgcaac    660
cacgtgagcc agcggacgtg tgtggcggag gagattctgg agtattgcga ggacccggta    720
ccttagtctc ccctggcggt ttctgtcata tgcgatgttc tcwctttatt cacttttttt    780
tgctaatgct tacagatata cagtatatgc atagcgcatt ctgataacac atatgtatat    840
tttatakgtg tacaatgtgt gttaaaacaa attcattgtg ttctctctgt ttcacaaggt    900
agaatataat cctatccttt tgatagtaat ttactcgcat acacgcttgt aaatcttgtt    960
ttcgtctcgt gtggttttga tctacattct tcttcatgta tgatttctag atgtgagagt   1020
aagtaggcaa gttatctctc gaatgaaatt cgaaatcagg caaatcagty attaacattt   1080
ctcccttctg tttccccagt acttctaaac cttgaacctg acctgaccta tggccttcct   1140
aacctctcta gtggagtcg tcagtggtcc atggcccacc catcctcctt acaacagtct   1200
tcggtgacct gatcatatgg cctctccatc ctctcaatga cctgacctca acccayggt   1260
```

```
cccccttct ttaggccaag tctttgcgga cctgacccaa acccgaggct tctctaaccc    1320
tcctctgatg agtttgtaat aaaaataacc ggcctggtga cccaagttct catgaatttg    1380
acttaatctg caattaatga cccgttagag tcctttcaat gatgtctgcc aaaagtagcg    1440
ttacattcca ttttttcttt cgaktawtag gccccagagt aattcttgac ctcaactttc    1500
taaaaaaaaa taygtatatt cagrgcaaga actattttca ttcatgttct gtcaatttct    1560
tyggcgtcat aatttctttc tatccttta ttaaacaaaa taaataaaag ataaccatac    1620
attaacaaag gtgtgataca aagacataaa agatatcaaa gttcagtact ttctttcgct    1680
ttttctattt ttatctttcg atttccgaa cgttttaaag tttctaactt ttatcccyct    1740
gtaaaaataa agttgacaga cgataataaa aagcaataat gttttagaat ctattccttt    1800
tttgtgatca cctgaatatc ttttttatat atacattatc gtattggaat cagatagatc    1860
agyacggyat atcagaatta attcgtaata aaaaaatgca tttcaataac tgaatttccg    1920 ataaaaaat ttcmcctgta tctgtctttt gcgaaacaat aaaagcattt caaatcgrg     1980 aaatatgaat ccttgcttgc aacagctg                                     2008
```

<210> SEQ ID NO 14
<211> LENGTH: 25
<212> TYPE: DNA
<213> ORGANISM: Artificial Sequence
<220> FEATURE:
<223> OTHER INFORMATION: Primer

<400> SEQUENCE: 14
tatgacagaa accgccaggg gagac                                            25

<210> SEQ ID NO 15
<211> LENGTH: 25
<212> TYPE: DNA
<213> ORGANISM: Artificial Sequence
<220> FEATURE:
<223> OTHER INFORMATION: Primer

<400> SEQUENCE: 15
aggtaccggg tcctcgcaat actcc                                            25

<210> SEQ ID NO 16
<211> LENGTH: 25
<212> TYPE: DNA
<213> ORGANISM: Artificial Sequence
<220> FEATURE:
<223> OTHER INFORMATION: Primer

<400> SEQUENCE: 16
ctggcggttt ctgtcatatg cgatg                                            25

<210> SEQ ID NO 17
<211> LENGTH: 25
<212> TYPE: DNA
<213> ORGANISM: Artificial Sequence
<220> FEATURE:
<223> OTHER INFORMATION: Primer

<400> SEQUENCE: 17
gtctcccctg gcggtttctg tcata                                            25

<210> SEQ ID NO 18
<211> LENGTH: 20
<212> TYPE: DNA
<213> ORGANISM: Artificial Sequence

```
<220> FEATURE:
<223> OTHER INFORMATION: Primer

<400> SEQUENCE: 18
acacaggaca gggcaagttc                                               20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tccctccaca aaaaccactc                                               20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
tctggggcct attaatcgaa                                               20

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
acgttcggaa aatcgaaaga t                                             21

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
gtgctgccac acacaggac                                                19

<210> SEQ ID NO 23
<211> LENGTH: 16
<212> TYPE: DNA
<213> ORGANISM: Artificial Sequence
<220> FEATURE:
<223> OTHER INFORMATION: Primer

<400> SEQUENCE: 23
gcacgccctc gtcaag                                                   16

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
tcaagaatta ctctggggcc ta                                            22
```

```
<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
ccagtaccgc ctgcatcc                                                   18

<210> SEQ ID NO 26
<211> LENGTH: 19
<212> TYPE: DNA
<213> ORGANISM: Artificial Sequence
<220> FEATURE:
<223> OTHER INFORMATION: Primer

<400> SEQUENCE: 26
ggctcaccag gtggtctct                                                  19

<210> SEQ ID NO 27
<211> LENGTH: 38
<212> TYPE: DNA
<213> ORGANISM: Artificial Sequence
<220> FEATURE:
<223> OTHER INFORMATION: Primer

<400> SEQUENCE: 27
taatacgact cactataggg atgcccactc agctgctt                             38

<210> SEQ ID NO 28
<211> LENGTH: 39
<212> TYPE: DNA
<213> ORGANISM: Artificial Sequence
<220> FEATURE:
<223> OTHER INFORMATION: Primer

<400> SEQUENCE: 28
taatacgact cactataggg ctaaggtacc gggtcctcg                            39
```

CRUSTACEAN ANDROGENIC GLAND HORMONE, ASSOCIATED PEPTIDES, AND USE THEREOF

CROSS-REFERENCE TO RELATED APPLICATIONS

This is a national phase entry under 35 U.S.C. §371 of International Patent Application PCT/EP2009/052587, filed Mar. 5, 2009, published in English as International Patent Publication WO 2009/109615 A1 on Sep. 11, 2009, which claims the benefit under Article 8 of the Patent Cooperation Treaty to U.S. Provisional Patent Application Ser. No. 61/033,830, filed Mar. 5, 2008.

TECHNICAL FIELD

The present invention relates to a novel crustacean androgenic gland hormone. More specifically, the invention relates to an androgenic gland hormone derived from *Penaeus monodon*. The invention relates further to the use of the hormone to influence the sex ratio in prawn and shrimp cultures, and to set up monosex cultures. It also relates to the use of the hormone and its gene or fragments thereof in sex determination.

BACKGROUND

Shrimp and prawn cultivation and trade is a very important activity all over the world. The main species under cultivation are *Penaeus monodon* (Giant tiger prawn, Jumbo tiger prawn, Jumbo tiger shrimp, Black tiger prawn, Blue tiger prawn, Grass shrimp . . . ), mainly cultivated in Asia, with an aquaculture production of about 600,000 tons in 2003; and *Penaeus vannamei* (Whiteleg shrimp, white shrimp), mainly cultivated in the Americas and in China and Thailand, with an aquaculture production that is comparable to *P. monodon*. For those species, aquaculture is far more important than capture.

Increasing demands for aquaculture production mean increasing pressure for the development of more efficient production systems.

As most *Penaeus* sp. are sexually dimorphic (Hansford and Hewitt, 1994), a lot of effort has been paid in setting up monosex cultures. In that respect, several groups have tried to develop reliable sex markers (Khamnamtong et al., 2006). Alternatively, monosex cultures could be obtained by in vitro secretion of androgenic sex hormone from the androgenic gland, as disclosed in U.S. Pat. No. 6,740,794. Although this may be an interesting approach, it is hampered by the fact that the structure of the androgenic gland hormone, or of the gene encoding, is not known. Recently, Manor et al. (2007) described an insulin-like gene that is exclusively expressed in the androgenic gland of the male Australian Crayfish *Cherax quadricarinatus*. This may be an interesting candidate gene, possibly coding for the androgenic gland hormone, but its effect has not yet been demonstrated. Moreover, no homologues in prawns or shrimps are known today. Searching for homologous sequences is hampered by the fact that only a limited number of prawn and shrimp sequences are available in the databases, and by the fact that the interspecies homology is probably low, if any.

Surprisingly, in an AFLP-based transcriptomic profiling experiment in the black tiger shrimp (*Penaeus monodon*), we identified two androgenic gland-specific DNA fragments homologous to isopod "androgenic gland hormone" and crayfish "insulin-like androgenic gland" factor. By further cDNA sequencing and RACE experiments, we identified four mRNAs, termed PmAGH1, PmAGH2, PmAGH3 and PmAGH4, most probably originating from a single gene by alternative splicing. Even more surprisingly, treatment of genetically female juvenile shrimp using recombinant Pm_AGH1, Pm_AGH2, PmAGH3 and/or PmAGH4, had masculinizing effects. Genetically male juvenile shrimp were feminized by dsRNA-mediated knock-down of Pm_AGH1, Pm_AGH2, PmAGH3 and/or PmAGH4.

DISCLOSURE

A first aspect of the invention is an isolated protein selected from the group consisting of SEQ ID NO:3, SEQ ID NO:6, SEQ ID NO:9 and SEQ ID NO:12, or a mutant or variant thereof. Preferably, the protein is isolated from a Penaeus species, more preferably it is isolated from *Penaeus monodon*. Mutants and variants as described herein are mutants and variants with at least 50% identity, as measured in a BLASTp (Altschul et al., 1997). Preferably, the mutants and variants are biologically active, as measured by their hormone effect (masculinization; or feminization when acting as a dominant negative compound). Even more preferably, the mutants and variants are retaining the masculinization capacity of the isolated proteins with SEQ ID NO:3, SEQ ID NO:6, SEQ ID NO:9 or SEQ ID NO:12.

Another aspect of the invention is a nucleic acid fragment, encoding a protein according to the invention. "Nucleic acid fragment," as used herein, can be any nucleic acid including, but not limited to, messenger RNA, single-stranded DNA, double-stranded DNA, including genomic DNA, possible with its intron-exon organization. In its simplest form, the nucleic acid fragment is limited to the coding sequence, but it may comprise other sequences such as, but not limited to, 5' and 3' untranslated sequences, regulatory sequences such as promoter and terminator sequences, and introns. Preferably, the nucleic acid fragment comprises SEQ ID NO:2, SEQ ID NO:5, SEQ ID NO:8 or SEQ ID NO:11 (coding sequences).

Still another aspect of the invention is a nucleic acid fragment, comprising SEQ ID NO:1, SEQ ID NO:4, SEQ ID NO:7 or SEQ ID NO:10 (mRNA) or SEQ ID NO:13 (gDNA), or its complement, or a functional fragment thereof. "A functional fragment" as used herein is, as a non-limiting example, a fragment that can be used as primer for detection, or a fragment that can be used as antisense RNA or as RNAi for down-regulating the expression.

Another aspect of the invention is the use of a protein according to the invention to modify the sex ratio in prawns or shrimps. Preferably, the prawns or shrimps belong to the family of Penaeidae, even more preferably, the prawn or shrimp is a Penaeus species, most preferably, the prawn or shrimp is *Penaeus monodon*.

Still another aspect of the invention is the use of a nucleic acid fragment according to the invention to modify the sex ratio in prawns or shrimps. Preferably, the prawns or shrimps belong to the family of Penaeidae, even more preferably, the prawn or shrimp is a Penaeus species, most preferably, the prawn or shrimp is *Penaeus monodon*.

Yet another aspect of the invention is the use of a nucleic acid sequence according to the invention to determine sex in prawns or shrimps. Preferably, the prawns or shrimps belong to the family of Penaeidae, even more preferably, the prawn or shrimp is a Penaeus species, most preferably, the prawn or shrimp is *Penaeus monodon*. Indeed, on the basis of the sequence presented, it is obvious for the person skilled in the art to develop primers that can be used to measure gene expression of the androgenic gland-specific gene.

Yet another aspect of the invention is a method of setting up a monosex culture in prawns or shrimps, comprising the use of a protein and/or a nucleic acid according to the invention. Preferably, the prawns or shrimps belong to the family of Penaeidae, even more preferably, the prawn or shrimp is a *Penaeus* species, most preferably, the prawn or shrimp is *Penaeus monodon*. Indeed, by injecting the protein into young post-larval animals, females can be converted into males. Alternatively, expression and/or injection of anti-sense RNA, dsRNA and/or RNAi will repress the expression of the androgenic gland-specific protein, and feminizes the animals. As an alternative, antibodies, preferably single chain antibodies or camelid antibodies or antibody fragments such as nanobodies against the proteins of the invention, can be used to feminize the prawns or shrimps. Using the purified protein, or fragments thereof, the generation of antibodies is a process known to the person skilled in the art.

Another aspect of the invention is a method of setting up a monosex culture in prawns or shrimps, comprising sex determination using a nucleic acid according to the invention. Preferably, the prawns or shrimps belong to the family of Penaeidae, even more preferably, the prawn or shrimp is a *Penaeus* species, most preferably, the prawn or shrimp is *Penaeus monodon*. Alternatively, a protein according to the invention could be used in sex determination too, especially in combination with an antibody against the protein according to the invention, as described above. Such antibody can be used, as a non-limiting example, in an ELISA assay to test the concentration of androgenic gland-specific protein present in the animal.

BRIEF DESCRIPTION OF THE DRAWING

FIG. 1: Schematic overview of the genomic DNA encoding the androgenic gland hormone, and the messenger RNAs derived from it by alternative splicing.

DETAILED DESCRIPTION

Examples

Materials and Methods to the Examples

Sampling

Tissue was dissected at the base of the fifth walking leg, where the androgenic gland is supposed to be situated, from mature males. Control tissue was dissected from the identical location in females. Muscle samples were taken from the tail of adult males and females. All samples were immediately snap frozen in liquid nitrogen and stored at −70° C. until RNA preparation.

cDNA-AFLP

Snap frozen androgenic gland samples (n=4), control surrounding tissue samples (n=2) and muscle samples (n=6) were pulverized using mortar and pestle under liquid nitrogen. Total RNA was isolated using the TRIzol reagent (Invitrogen). RNA quality was assessed spectrophotometrically (Nanodrop) and by gel electrophoresis. High quality RNA (2.5 μg) was converted to double-stranded cDNA using a biotinylated oligo-dT primer. After purification of the ds cDNA (Qiaquick PCR purification kit, Qiagen), the quality and yield were analyzed by gel electrophoresis.

AFLP templates were prepared by restriction digest of the ds cDNA using BstYI. The 3' end fragments were isolated using strepavidin-coated magnetic Dynabeads (Dynal) and further digested using MseI. Restriction site-specific adapters were ligated to the ends of the fragments.

The adapter-ligation mixture was diluted two-fold to a total volume of 100 μl. Amplification using a BstYI-specific primer with either a T (BstYI-T+0) or C (BstYI-C+0) at its 3' end in combination with an MseI-specific primer divided the set of fragments in two. Specific amplification of 5 μl of the 600-fold diluted pre-amplification mixtures was performed using the $^{33}$P labelled BstYI-C/T primer with one additional selective nucleotide at its 3' end in combination with the MseI primer with two selective nucleotides. In this setting, 128 primer combinations were needed to screen the full set of transcript fragments.

After amplification, the samples were separated on a 5% polyacrylamide sequencing gel. A $^{33}$P labelled 10 bp sizing standard was included. After running and vacuum-drying on whatmann paper, the gel was scanned in a phosphor-imager.

Sequence Analysis of cDNA-AFLP Fragments.

When cDNA-AFLP fragments were to be cut from the gel for sequence analysis, the gel was exposed on a Biomax MR autoradiogram (Kodak). Gels were overlaid with the developed film and the relevant fragments were cut from the gel. DNA was dissolved in TE buffer (10 mM Tris, 0.1 mM EDTA) and reamplified using the selective BstYI and MseI primers. Amplification was checked by gel electrophoresis and fragments were directly sequenced using either the selective BstYI or MseI primer.

Homology Search Using Obtained Sequences.

The non-redundant protein sequence database and an in-house compiled DNA sequence database containing all available DNA sequences from invertebrates were searched for sequences homologous to the sequence of the cDNA-AFLP fragment. An in-house-developed algorithm first searched the protein database for sequences homologous to the translated (in all six possible reading frames) query sequence (BLASTX search). When no homology was found, the invertebrate DNA database was searched for homologous DNA sequences (BLASTN search). When homology was identified to a DNA sequence, a BLASTX search was performed with this hit. When no homology was found in the invertebrate DNA database, a TBLASTX search was performed, in which homology was searched in the translated DNA database using the translated query sequence.

RACE Analysis of Putative Androgenic Gland Hormone Genes.

Rapid Amplification of cDNA Ends (RACE) analysis was performed using the BD SMART RACE cDNA amplification kit (BD Biosciences). High-quality total RNA (1 μg) from androgenic gland tissue was converted to 5' RACE-ready cDNA and 3' RACE-ready RACE cDNA according to the manufacturer's instructions. 5' and nested 5' RACE were performed using AGHRACE_Rev1 (5'-TATGACAGAAAC-CGCCAGGGGAGAC-3' (SEQ ID NO:14)) and AGHRA-CE_Rev2 (5'-AGGTACCGGGTCCTCGCAATACTCC-3' (SEQ ID NO:15)) primers, respectively. 3' and nested 3' RACE were performed using AGHRACE_Fw1 (5'-CTG-GCGGTTTCTGTCATATGCGATG-3' (SEQ ID NO:16)) and AGHRACE_Fw2 (5'-GTCTCCCCTGGCGGTTTCT-GTCATA-3' (SEQ ID NO:17)) primers, respectively. Only one distinct fragment was amplified in both the 5' and nested 5' RACE while two distinct fragments were amplified in both the 3' and 3' nested RACE. Fragments were isolated from the gel and cloned using the TOPO TA cloning kit for sequencing (Invitrogen). Cloned fragments were sequenced using standard T7 and SP6 primers. Sequences were manually curated and assembled using the software packages phredPhrap and consed (Ewing et al., 1998; Ewing and Green, 1998; Gordon et al., 1998).

Based on the consensus cDNA sequence obtained in the RACE experiments, primers were designed for amplification of the full-length cDNA. Forward primers AGHRT_3 (5'-ACACAGGACAGGGCAAGTTC-3' (SEQ ID NO:18)) and AGHRT_1 (5'-TCCCTCCACAAAAACCACTC-3' (SEQ ID NO:19)) were used in combination with reverse primers AGHRT_12 (5'-TCTGGGGCCTATTAATCGAA-3' (SEQ ID NO:20)) and AGHRT$_{16}$ (5'-ACGTTCGGAAAATC-GAAAGAT-3' (SEQ ID NO:21)). The sizes of the PCR fragments were according to what was expected from the RACE experiments and sequencing of the fragments confirmed the sequences obtained previously by RACE.

Genomic Sequencing of Putative Androgenic Gland Hormone Genes.

Using primers AGHFULL2_FW (5'-GTGCTGCCACA-CACAGGAC_-3' (SEQ ID NO:22)) and AGHPC3_FW (5'-GCACGCCCTCGTCAAG-3' (SEQ ID NO:23)) in combination with primer AGHFULL2_REV (5'-TCAAGAATTACTCTGGGGCCTA-3' (SEQ ID NO:24)) and primer AGH_indel1 (5'-CCAGTACCGCCTGCATCC-3' (SEQ ID NO:25)) in combination with primer AGH_indel2 (5'-GGCTCACCAGGTGGTCTCT-3' (SEQ ID NO:26)), we PCR amplified overlapping fragments of the AGH gene on genomic DNA. Additional sequence information was obtained using the Genome Walker Universal Kit (Clontech). Genomic DNA was isolated from several female shrimp and pooled. DNA libraries were prepared according to the manufacturer's instructions and primary 5' and 3' amplification reactions were performed using primers AGHRACE_REV1 and AGHRACE_FW1 (see above), respectively. Nested amplification reactions were performed using primers AGH-RACE_REV2 and AGHRACE_FW2 (see above), respectively. A partial genomic sequence, including the complete 3' UTR region of the mRNA sequences up until the polyA-tail, was assembled using the software packages phredPhrap and consed.

Cloning and Recombinant Protein Expression Putative Androgenic Gland Hormone Genes.

The full-length coding sequence was expressed in a yeast host (Pichia pastoris), to ensure correct folding and glycosylation of the recombinant protein.

dsRNA Production.

Using PCR primers AGH_CDS_T7_Fw (5'-TAATAC-GACTCACTATAGGGATGCCCACTCAGCTGCTT3' (SEQ ID NO:27)) and AGH_CDS_T7_Rev (5'-TAATAC-GACTCACTATAGGGCTAAGGTACCGGGTCCTCG-3' (SEQ ID NO:28)), we generated a PCR fragment incorporating a T7 promotor sequence at both. This fragment was used as a T7 RNA polymerase template for dsRNA production using the Megascript RNAi kit (Ambion).

Sex Reversal Experiments in Juvenile *P. monodon* Shrimp by Injection of Recombinant AGH.

Groups of young post-larval animals (PL30-PL60) are injected with 120 ng of the recombinant AGH every third day. Group 1 receives injections covering the period of PL30 to PL60. Group 2 receives injections covering the period of PL30 to PL45. Finally, group 3 receives injections covering the period of PL45 to PL60. At PL150, phenotypic sex is assessed by visual inspection and histology while genotypic sex is determined at the DNA level using a PCR-based sex marker as disclosed in PCT/EP2007/054041.

Sex Reversal Experiments in Juvenile *P. monodon* Shrimp by Injection of AGH-Specific dsRNA.

Groups of young post-larval animals (PL30-PL60) are injected with 0.5 µg of AGH dsRNA every third day. Group 1 receives injections covering the period of PL30 to PL60. Group 2 receives injections covering the period of PL30 to PL45. Finally, group 3 receives injections covering the period of PL45 to PL60. At PL150, phenotypic sex is assessed by visual inspection and histology while genotypic sex is determined at the DNA level using a PCR-based sex marker as disclosed in PCT/EP2007/054041.

Example 1

Identification of *Penaeus monodon* Androgenic Gland Hormones

Transcript profiling of all possible cDNA-AFLP primer combinations (128 PC) was performed on androgenic gland tissue samples (male; n=4), surrounding tissue control samples (female; n=2) and female and male muscle samples (n=3 each). By visual inspection of the cDNA-AFLP gels, we selected 355 androgenic gland specific fragments. We obtained sequence information for 254 (71.6%) of these fragments. Homology searches indicated that at least 47 (18.5%) of these were identical (BLASTX alignment showing at least 75% identities) to bacterial sequences (*Propionibacterium acnes*). This is most likely due to a bacterial infection of the androgenic glands in the sampled animals.

Two cDNA-AFLP fragments were found to be homologous to "insulin-like androgenic gland factor" from the red-claw crayfish (*Cherax quadricarinatus*): BC4M21M263.5 and BC4M34M404.4.

RACE analysis, followed by full-length cDNA amplification and sequencing resulted in the identification of four cDNA sequences PmAGH1 (SEQ ID NO:1), PmAGH2 (SEQ ID NO:4), PmAGH3 (SEQ ID NO:7) and PmAGH4 (SEQ ID NO:10). Genomic sequencing of a part of the gene (SEQ ID NO:13) indicated that all four of these cDNAs originate by alternative splicing from a single gene.

Fragment BC4M21M263.5 corresponds to a 234 bp BstYI-MseI restriction fragment originating from PmAGH1 and PmAGH3, while fragment BC4M34M404.4 corresponds to a 372 bp BstYI-MseI restriction fragment originating from PmAGH2 and PmAGH4.

Homology search with the full cDNA sequences revealed no significant homology on the nucleotide level. On the protein level, homology was again found with the crayfish "insulin-like androgenic gland factor" (32% identity) and to a lesser extent with the androgenic gland hormones from the isopods *Armadillidium vulgare*, *Porcelio scaber* and *Porcelio dilatatus* (between 29% and 26% identity).

Example 2

Sex Reversal in Juvenile *P. monodon* Using Recombinant Pm_AGH1, Pm_AGH2, Pm_AGH3 and/or Pm_AGH4

Administration of recombinant PenMon_AGH1 and PenMon_AGH2 to juvenile *P. monodon* is able to masculinize genetic females.

Example 3

Sex Reversal in Juvenile *P. monodon* Using dsRNA-Mediated Knock-Down of the Androgenic Gland Hormone Gene Administration of dsRNA targeting PenMon_AGH1/2 is able to knock down gene expression of both variants and feminized genetically male juvenile *P. monodon*.

REFERENCES

Altschul S. F., T. L. Madden, A. A. Schäffer, J. Zhang, Z. Zhan, W. Miller, and D. J. Lipman (1997). Gapped BLAST and PSI-BLAST: a new generation of protein database search programs. *Nucl. Acids Res.* 25:3389-3402.

Ewing B. and P. Green (1998). Base-calling of automated sequencer traces using phred. II. Error probabilities. *Genome Research* 8:186-194.

Ewing B., L. Hillier, M. C. Wendel, and P. Green (1998). Base-calling of automated sequencer traces using phred. I. Accuracy assessment. *Genome Research* 8:175-185.

Gordon D., C. Abajian, and P. Green (1998). Consed: a graphical tool for sequence finishing. *Genome Research* 8:195-202.

Hansford S. W. and D. R. Hewitt (1994). Growth and nutrient digestibility by male and female *Penaeus monodon*: evidence of sexual dimorphism. *Aquaculture* 125:147-154.

Khamnamtong B., S. Thumrungtanakit, S. Klingbunga, T. Aoki, I. Hirono, and P. Menasveta (2006). Identification of sex-specific expression markers in the giant tiger shrimp (*Penaeus monodon*). *J. Biochem. Mol. Biol.* 39:37-45.

Manor R., S. Weil, S. Oren, L. Glazer, E. D. Aflalo, T. Ventura, V. Chalifa-Caspi, M. Lapidot, and A. Sagi (2007). Insulin and gender: an insulin-like gene expressed exclusively in the androgenic gland of the male crayfish. *Gen. Comp. Endocrinol.* 150:326-336.

---

What is claimed is:

1. An isolated protein having an amino acid sequence selected from the group consisting of SEQ ID NO: 3, SEQ ID NO: 6, SEQ ID NO: 9 and SEQ ID NO: 12.

2. A method of modifying the sex ratio in prawns or shrimps in a culture, the method comprising:
injecting the protein according to claim 1 into prawn or shrimp of the culture to modify the sex ratio in prawns or shrimps in the culture.

3. The method according to claim 2, wherein said prawn or shrimp belongs to the family of Penaeidae.

4. The method according to claim 3, wherein said prawn or shrimp is *Penaeus monodon*.

5. The protein of claim 1, having the amino acid sequence of SEQ ID NO: 3.

6. A method of modifying the sex ratio in prawns or shrimps in a culture, the method comprising:
injecting the protein of claim 5 into prawn or shrimp of the culture to modify the sex ratio in prawns or shrimps in the culture.

7. The protein of claim 1, having the amino acid sequence of SEQ ID NO: 6.

8. A method of modifying the sex ratio in prawns or shrimps in a culture, the method comprising:
injecting the protein of claim 7 into prawn or shrimp of the culture to modify the sex ratio in prawns or shrimps in the culture.

9. The protein of claim 1, having the amino acid sequence of SEQ ID NO: 9.

10. A method of modifying the sex ratio in prawns or shrimps in a culture, the method comprising:
injecting the protein of claim 9 into prawn or shrimp of the culture to modify the sex ratio in prawns or shrimps in the culture.

11. The protein of claim 1, having the amino acid sequence of SEQ ID NO: 12.

12. A method of modifying the sex ratio in prawns or shrimps in a culture, the method comprising:
injecting the protein of claim 11 into prawn or shrimp of the culture to modify the sex ratio in prawns or shrimps in the culture.

* * * * *